United States Patent [19]

Krause

[11] Patent Number: 4,833,247

[45] Date of Patent: May 23, 1989

[54] PROCESS FOR THE PRODUCTION OF 2-BENZYL FATTY ACIDS

[75] Inventor: Horst-Juergen Krause, Duesseldorf, Fed. Rep. of Germany

[73] Assignee: Henkel Kommanditgesellschaft auf Aktien, Duesseldorf, Fed. Rep. of Germany

[21] Appl. No.: 172,109

[22] Filed: Mar. 23, 1988

[30] Foreign Application Priority Data

Mar. 30, 1987 [DE] Fed. Rep. of Germany ....... 3710516

[51] Int. Cl.$^4$ ................. C07D 265/30; C07D 295/10; C07D 207/08
[52] U.S. Cl. .................................... 544/171; 544/395; 546/238; 548/573; 560/19; 560/55; 560/103; 562/433; 562/471; 562/493
[58] Field of Search ................ 544/171, 395; 546/238; 548/573; 560/19, 55, 103; 562/433, 471, 493

[56] References Cited

PUBLICATIONS

V. H. Wallingford et al., J. Am. Chem. Soc. 64, 580–582 (1942).
H. L. Wehrmeister, J. Org. Chem. 27, 4418–4420 (1962).

Primary Examiner—Mary C. Lee
Assistant Examiner—J. Richter
Attorney, Agent, or Firm—Ernest G. Szoke; Wayne C. Jaeschke; Henry E. Millson, Jr.

[57] ABSTRACT

A process for the production of 2-benzyl fatty acids and esters thereof corresponding to the following formula

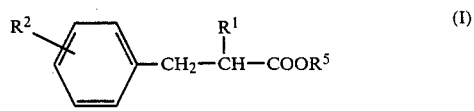

comprising reacting 2-fatty alkyl-4,4-dimethyl-2-oxazolines with benzaldehydes corresponding to the formula $R^2$—$C_6H_4$—CHO to form 2-(1-benzylidene)-fatty alkyl-4,4-dimethyl-2-oxazolines, catalytically hydrogenating the products of this reaction to the 2-(1-benzyl)-fatty alkyl-4,4-dimethyl oxazolines and converting the products thus formed by acid-catalyzed hydrolysis or solvolysis with an alcohol of the formula $R^5OH$ into the 2-benzyl fatty acids or esters thereof. Amidosulfonic acid gives particularly high yields as catalyst for the reaction of the 2-fatty alkyl-4,4-dimethyl-2-oxazolines with the benzaldehydes.

10 Claims, No Drawings

PROCESS FOR THE PRODUCTION OF 2-BENZYL FATTY ACIDS

BACKGROUND OF THE INVENTION

1. Field of the Invention:

This invention relates to a new process for the production of 2-benzyl fatty acids.

2. Statement of Related Art:

Modified fatty acids, more especially saturated fatty acids with a branch in the otherwise linear fatty chain, show certain advantages in the terms of practical application over the natural, linear fatty acids. These advantages are attributable, inter alia, to the fact that, through the introduction of a branch into the molecule, molecular weight and boiling point are increased while, at the same time, volatility and melting point are reduced. These advantages are shown not only by the fatty acids themselves, but also by soaps, esters, amides, nitriles, amines, and derivatives thereof obtainable from the fatty acids. Accordingly, there has been no shortage of attempts to introduce substituents into the fatty acid molecule.

Attempts have also been made to introduce benzyl groups into the α-position (2-position) of fatty acids. V. H. Wallingford et al. (in J. Am. Chem. Soc. 64 (1942), pgs. 580 to 582) attempted to prepare α-substituted fatty acids, including 2-benzylstearic acid, by alkylation of malonic esters, hydrolysis, and decarboxylation. This process is too complicated for the commercial production of 2-benzyl fatty acids.

H. L. Wehrmeister (in J. Org. Chem. 27 (1962), pgs. 4418 to 4420) described a process for the production of short-chain 2-benzylidenealkane acids in which 2-alkyl-4,4-dimethyl-2-oxazolines are condensed with benzaldehyde and the 2-(1-benzylidene)-alkyl-4,4-dimethyl-2-oxazoline obtained is converted by hydrolysis into the 2-benzylidenealkane acid. This process can only be applied to 2-fatty alky-4,4-dimethyl-2-oxazolines with very poor yields of less than 40%, if at all, using the catalysts described in this publication for the condensation with the benzaldehyde.

DESCRIPTION OF THE INVENTION

Other than in the operating examples, or where otherwise indicated, all numbers expressing quantities of ingredients or reaction conditions used herein are to be understood as modified in all instances by the term "about".

It was only the discovery of suitable reaction conditions and a catalyst suitable for this reaction that made it possible to provide a new process for the production of 2-benzyl fatty acids suitable for use on an industrial scale.

The present invention relates to a new process for the production of 2-benzyl fatty acids and esters thereof corresponding to the following formula

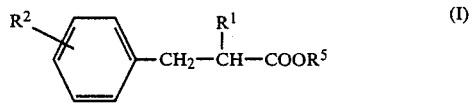

in which $R^1$ is a linear $C_4$–$C_{20}$ alkyl group; $R^2$ is hydrogen, a $C_1$–$C_4$ alkyl group, chlorine, bromine, a nitro group, a group $—OR^3$, where $R^3$ is a $C_1$–$C_4$ alkyl group, or a group $—NR^3R^4$, where $R^3$ and $R^4$ are $C_1$–$C_4$ alkyl groups or, together with the nitrogen atom, form a pyrrolidine, piperidine, morpholine or piperazine ring or $R^3$ is hydrogen and $R^4$ is a $C_1$–$C_4$ acyl group; and $R^5$ is hydrogen or a $C_1$–$C_4$ alkyl group, comprising the steps of:

A. reacting a 2-fatty alkyl-4,4-dimethyl-2-oxazoline corresponding to the following formula

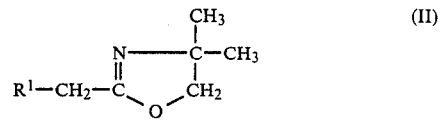

with a benzaldehyde corresponding to the formula $R^2—C_6H_4—CHO$ to form a 2-(1-benzylidene)-fatty alkyl-4,4-dimethyl-2-oxazoline corresponding to the following formula

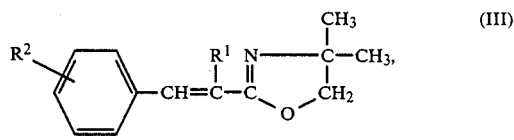

B. catalytically hydrogenating the compound of formula III to the corresponding 2-(1-benzyl)-fatty alkyl-4,4-dimethyl oxazoline, and C. converting the 2-(1-benzyl)-fatty alkyl-4,4-dimethyl oxazoline by acid-catalyzed hydrolysis or solvolysis with an alcohol corresponding to the formula $R^5OH$ into a 2-benzyl fatty acid or ester of formula (I).

In formulae (II) and (III) above, $R^1$ and $R^2$ have the same meaning as in formula (I). $R^2$ is preferably hydrogen.

The preparation of the 2-fatty alkyl-4,4-dimethyl-2-oxazolines of formula (II) above is known. A suitable process for their preparation from $C_6$–$C_{18}$ fatty acids and 2-amino-2-methylpropanol is described, for example, by S. Serota et al. in J. Org. Chem. 46 (1981), pgs. 4147 to 4151.

Benzaldehydes corresponding to the formula $R^2—C_6—H_4CHO$ are known from the literature and, in most cases, are commercially available.

The reaction of the 2-fatty alkyl-4,4-dimethyl-2-oxazolines corresponding to formula (II) with benzaldehydes corresponding to the formula $R^2—C_6H_4—CHO$ is carried out in the presence of amidosulfonic acid as catalyst. The reaction is preferably carried out at a temperature of from 130° to 160° C. in an inert solvent which enables the water formed during the condensation to be azeotropically removed. Alkylbenzenes having a boiling point above 130° C., for example ethylbenzene, xylenes or cumene, are preferably used as the inert solvent. Cumene is particularly suitable. The 2-fatty alkyl-4,4-dimethyl-2-oxazoline is preferably initially introduced with part (10 to 30%) of the benzaldehyde and with the catalyst (approx. 0.1 mole amidosulfonic acid per mole oxazoline) and the remaining benzaldehyde (up to a quantity of, in all, approx. 1.1 mole per mole oxazoline) is gradually added during the condensation and azeotropic removal of the water.

Where this procedure is adopted, a yield of 85 to 95% (based on the oxazoline) of 2-(1-benzylidene)-fatty alkyl-4,4-dimethyl-2-oxazoline is obtained, enabling the process to be carried out on an industrial scale.

The hydrogenation of the 2-(1-benzylidene)-fatty alkyl-4,4-dimethyl-2-oxazolines is carried out in an inert solvent, for example in an alkylbenzene such as toluene, xylene, ethylbenzene or cumene, or without a solvent, in the presence of a hydrogenation catalyst, for example a catalyst from the platinum group. Palladium on a support, for example Pd-carbon containing approximately 5% by weight Pd on active carbon is particularly suitable. This catalyst is used in a quantity of approximately 0.1 part by weight per part by weight of the oxazoline. Another particularly suitable hydrogenation catalyst is highly active nickel, for example in the form of Raney nickel or commercial "Girdler Nickel G49B". Where Pd-carbon is used, the hydrogenation is carried out at a temperature of from 70° to 100° C. Where active nickel catalysts are used, a somewhat higher temperature of 100° to 130° C. is necessary to achieve complete hydrogenation of the double bond in an equally short time. The hydrogenation reaction is exothermic so that, in the case of relatively large batches, cooling is advisable to maintain the optimal hydrogenation temperature. Under the described conditions, yields of 85 to 95% of 2-(1-benzyl)-fatty alkyl-4,4-dimethyl-2-oxazolines are obtained.

It has proven to be advisable to introduce the 2-(1-benzylidene)-fatty alkyl-4,4-dimethyl-2-oxazolines corresponding to formula (II) into the hydrogenation reaction without prior purification (e.g. by distillation) and only to purify the 2-(1-benzyl)-fatty alkyl-4,4-dimethyl-2-oxazolines by distillation on completion of the hydrogenation.

The acid-catalyzed hydrolysis of the 2-(1-benzyl)-fatty alkyl-4,4-dimethyl-2-oxazoline is carried out by boiling with aqueous mineral acids, preferably with concentrated aqueous hydrochloric acid. Water-insoluble 2-benzyl fatty acid and the water-soluble salt of 2-amino-2-methyl propanol are formed. The 2-benzyl fatty acids can readily be separated off after cooling of the reaction mixture and, after washing with water and drying, are sufficiently pure for most applications. If necessary, however, they can be purified by distillation or, in the case of the 2-benzyl fatty acids based on fatty acids containing 14 and more carbon atoms ($R^1 = C_{12}H_{25}$ to $C_{20}H_{41}$), by recrystallization.

One method for directly preparing 2-benzyl fatty acid esters of lower $C_1$–$C_4$ alcohols from the 2-(1-benzyl)-fatty alkyl-4,4-dimethyl-2-oxazolines is by solvolysis in an alcohol $R^5OH$, where $R^5$ is a $C_1$–$C_4$ alkyl group, in the presence of a mineral acid. Thus, direct solvolysis to the 2-(1-benzyl)-fatty acid methyl esters is carried out in methanol/HCl for example. Suitable acidic catalysts are any of the mineral acids and low molecular weight sulfonic acids known for this purpose, although hydrochloric acid is preferred.

The 2-amino-2-methyl propanol can be released from the aqueous phase of the reaction mixture accumulating during the hydrolysis by alkalization, for example with an alkali metal hydroxide, and recovered. If it is desired to work up this aqueous phase and to re-use the 2-amino-2-methyl propanol, which is essential for industrial production, sulfuric acid should not be used as the hydrolysis catalyst because it reacts with the 2-amino-2-methyl propanol to form aziridines.

The 2-benzyl fatty acids and esters of formula I are used as components in lubricating oils and greases. The 2-benzyl fatty acids and esters may also be esterified or transesterified respectively with polyols such as glycerine, trimethylolpropane or pentaerythrit in a manner known from linear fatty acids in order to obtain useful lubricating oil components.

The following Examples are intended to illustrate the invention without limiting it in any way.

EXAMPLES

1. Preparation of 2-fatty alkyl-4,4-dimethyl-2-oxazolines corresponding to formula (II) (general procedure)

2 moles of 2-amino-2-methyl-1-propanol were introduced into a stirring apparatus equipped with a distillation column, dropping funnel and gas inlet pipe. 1 mole of fatty acid was then slowly added dropwise (exothermic reaction).

The reaction mixture was then heated with stirring under nitrogen to 120° to 140° C., the water of reaction being continuously distilled off azeotropically until a vapor temperature of 105° C. had been reached (amide formation).

The reaction temperature was then increased to 180° C., whereupon more water split off (oxazoline formation).

Heating was continued until a vapor temperature of 165° C. (pure aminomethyl propanol (AMP)) had been reached. Excess AMP was then distilled off in a jet vacuum and the resulting 2-fatty alkyl-4,4-dimethyl-2-oxazoline subjected to fractional distillation.

The yield of pure 2-fatty alkyl-4,4-dimethyl-2-oxazoline was more than 85%.

The analytical data of the 2-fatty alkyl-4,4-dimethyl-2-oxazolines corresponding to formula (II) obtained in this way are also shown in Table I.

TABLE I

| No. | Starting fatty acid | $R^1$ | Boiling point | $n_D^{20}$ |
| --- | --- | --- | --- | --- |
| 1.1 | caprylic acid | 1-hexyl | 113° C. (2 mbar) | 1.4401 |
| 1.2 | capric acid | 1-octyl | 140° C. (12 mbar) | 1.4442 |
| 1.3 | lauric acid | 1-decyl | 112° C. (1 mbar) | 1.4498 |
| 1.4 | palmitic acid | 1-tetradecyl | 141° C. (0.3 mbar) | 1.4522 |
| 1.5 | stearic acid | 1-hexadecyl | 167° C. (0.001 mbar) | 1.4527 |

2.

Preparation of 2-(1-benzylidene)-fatty alkyl-4,4-dimethyl-2-oxazolines corresponding to formula (III) (general procedure)

1 mole 2-alkyl-4,4-dimethyl-2-oxazoline, 220 ml cumene, 10 g amidosulfonic acid and 0.2 mole benzaldehyde were introduced into a stirring vessel equipped with a water separator, reflux condenser and dropping funnel. The mixture was heated under nitrogen with stirring to the reflux temperature (160° C.). 0.9 mole benzaldehyde was then added dropwise over a period of 1 hour and the water of reaction formed azeotropically distilled off. On completion of the reaction, the reaction mixture was cooled, washed until neutral with 50 ml aqueous sodium hydrogen carbonate solution, the aqueous phase separated off, and the organic phase distilled.

The solvent and the excess benzaldehyde were distilled off in a water jet pump vacuum (15 torr).

The reaction product was then distilled in an oil pump vacuum in a thin-layer evaporator.

The analytical data of the products corresponding to formula (III) obtained in this way are shown in Table II:

TABLE II

| No. | Starting oxazoline | R¹ | R² | Boiling point (thin-layer evaporator) | $n_D^{20}$ | Yield (% of theoretical) |
|---|---|---|---|---|---|---|
| 2.1 | Example 1 | 1-hexyl | H | 130° C. (0.01 mbar) | 1.5330 | 90% |
| 2.2 | Example 2 | 1-octyl | H | 150° C. (0.01 mbar) | 1.5295 | 91% |
| 2.3 | Example 3 | 1-decyl | H | 170° C. (0.01 mbar) | 1.5223 | 85% |
| 2.4 | Example 4 | 1-tetradecyl | H | 180° C. (0.01 mbar) | 1.5135 | 91% |
| 2.5 | Example 5 | 1-hexadecyl | H | 200° C. (0.01 mbar) | | 88% |

3. Preparation of 2-(1-benzyl)-fatty alkyl-4,4-dimethyl-2-oxazolines by catalytic hydrogenation of 2-(1-benzylidene)-fatty alkyl-4,4-dimethyl-2-oxazolines (general procedure)

The 2-(1-benzylidene)-fatty alkyl-4,4-dimethyl-2-oxazolines were hydrogenated with the same quantity by weight of cumene as solvent in a stirrer-equipped hydrogenation autoclave in the presence of 10% by weight of a palladium-on-carbon catalyst (5% Pd on carbon) at 80° C. and 20 bar hydrogen.

The compounds corresponding to general formula (IV)

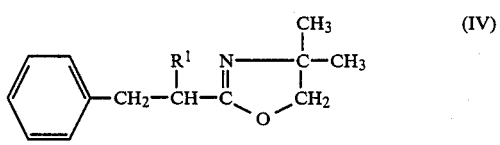

(IV)

were obtained, their analytical data being as follows (Table III)

TABLE III

| No. | Starting oxazoline | R¹ | Boiling point (thin-layer evaporator) | $n_D^{20}$ | Yield |
|---|---|---|---|---|---|
| 3.1 | Example 2.1 | 1-hexyl | 130° C. (0.01 mbar) | 1.4920 | 90% |
| 3.2 | Example 2.2 | 1-octyl | 140° C. (0.01 mbar) | 1.4876 | 93% |
| 3.3 | Example 2.3 | 1-decyl | 170° C. (0.01 mbar) | 1.4875 | 93% |
| 3.4 | Example 2.4 | 1-tetradecyl | 180° C. (0.01 mbar) | 1.4846 | 91.1% |
| 3.5 | Example 2.5 | 1-hexadecyl | 200° C. (0.01 mbar) | 1.4840 | 85% |

4. Preparation of (±) 2-benzyl fatty acids by hydrolysis of 2-(1-benzyl)-fatty alkyl-4,4-dimethyl-2-oxazolines (general procedure)

In a stirring apparatus equipped with a reflux condenser and gas inlet pipe for nitrogen, 500 ml concentrated hydrochloric acid were added to 1 mole of the particular 2-(1-benzyl)-fatty alkyl-4,4-dimethyl-2-oxazoline, followed by heating with stirring for 20 hours to the reflux temperature under nitrogen as inert gas.

After cooling, the oily phase (2-benzyl fatty acid) was separated off, washed with water and distilled in an oil pump vacuum in a thin-layer evaporator. In many cases, the acids were obtained in such pure form that distillation was not necessary.

Beyond R¹=1-tetradecyl the acids actually crystallize out after cooling at 20° C. They are filtered off under suction, washed with water until neutral and optionally recrystallized.

The aqueous solutions containing the 2-amino-2-methyl-1-propanol (AMP) hydrochloride can be worked up to recover the AMP.

The products corresponding to formula (I) shown in Table IV were obtained.

TABLE IV

| No. | Starting oxazoline | R¹ | Boiling point (thin-layer evaporator)/ melting point | $n_D^{20}$ | Yield |
|---|---|---|---|---|---|
| 4.1 | 3.1 | 1-hexyl | 140° C. (0.01 mbar) | 1.4975 | 97% |
| 4.2 | 3.2 | 1-octyl | 160° C. (0.01 mbar) | 1.4949 | 98% |
| 4.3 | 3.3 | 1-decyl | 180° C. (0.01 mbar) | 1.4923 | 99% |
| 4.4 | 3.4 | 1-tetradecyl | Mp.: 46° C. | | 96% |
| 4.5 | 3.5 | 1-hexadecyl | Mp.: 55° C. | | 98% |

The structure of the compounds was confirmed by nuclear resonance spectrometry (1 H-NMR). The composition of all the compounds listed in Table (I) to (IV) was confirmed by analytical determination of the C, H, and N contents.

I claim:

1. A process for the preparation of a 2-benzyl fatty acid or ester thereof corresponding to the following formula

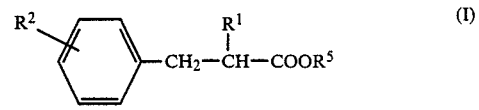

(I)

in which R¹ is a linear $C_4$–$C_{20}$ alkyl group; R² is hydrogen, a $C_1$–$C_4$ alkyl group, chlorine, bromine, a nitro group, a group —OR³, where R³ is a $C_1$–$C_4$ alkyl group, or a group —NR³R⁴, where R³ and R⁴ are $C_1$–$C_4$ alkyl groups, or together with the nitrogen atom, form a pyrrolidine, piperidine, morpholine or piperazine ring or R³ is hydrogen and R⁴ is a $C_1$–$C_4$ acyl group; and R⁵ is hydrogen or a $C_1$–$C_4$ alkyl group, comprising the steps of:

A. reacting a 2-fatty alkyl-4,4-dimethyl-2-oxazoline corresponding to the following formula

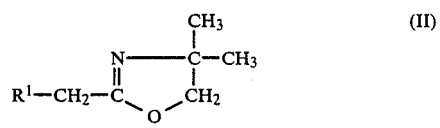

(II)

with a benzaldehyde corresponding to the formula R²—C₆H₄—CHO in the presence of amidosulfonic acid as catalyst to form a 2-(1-benzylidene)-fatty alkyl-4,4-dimethyl-2-oxazoline corresponding to the following formula

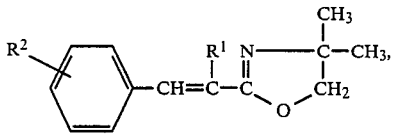

B. catalytically hydrogenating the compound of formula III to the corresponding 2-(1-benzyl)-fatty alkyl-4,4-dimethyl oxazoline, and C. converting the 2-(1-benzyl)-fatty alkyl-4,4-dimethyl oxazoline by acid-catalyzed hydrolysis or solvolysis with an alcohol corresponding to the formula $R^5OH$ into a 2-benzyl fatty acid or ester of formula (I), wherein in formulae (II), (III), and $R^5OH$ above, $R^1$, $R^2$ and $R^5$ have the same meaning as in formula (I).

2. The process of claim 1 wherein step A is carried out at a temperature of from about 130° to about 160° C. in an inert solvent which forms an azeotrope with water.

3. The process of claim 2 wherein the inert solvent is an alkyl benzene.

4. The process of claim 2 wherein the inert solvent is cumene.

5. The process of claim 1 wherein in step B the catalyst is a metal from the platinum group or is an active nickel catalyst.

6. The process of claim 5 wherein in step B the catalyst is a palladium catalyst and the hydrogenation temperature is in the range of from about 70° to about 100° C.

7. The process of claim 5 wherein in step B the catalyst is an active nickel catalyst and the hydrogenation temperature is in the range of from about 100° to about 130° C.

8. The process of claim 1 wherein step C is an acid-catalyzed hydrolysis wherein the acid is a mineral acid.

9. The process of claim 8 wherein the mineral acid is hydrochloric acid.

10. The process of claim 1 wherein step C is a solvolysis reaction carried out in methanol/HCl.

* * * * *